United States Patent
Tsuzaki et al.

(10) Patent No.: US 7,387,805 B2
(45) Date of Patent: Jun. 17, 2008

(54) FLAVONOID SOLUBILIZION AGENT AND METHOD OF SOLUBILIZING FLAVONOID

(75) Inventors: Shinichi Tsuzaki, Izumisano (JP); Satoshi Wanezaki, Izumisano (JP); Hideo Araki, Izumisano (JP)

(73) Assignee: Fuji Oil Company, Limited, Osaka (JP)

( * ) Notice: Subject to any disclaimer, the term of this patent is extended or adjusted under 35 U.S.C. 154(b) by 279 days.

(21) Appl. No.: 10/559,730

(22) PCT Filed: Jun. 24, 2004

(86) PCT No.: PCT/JP2004/008864

§ 371 (c)(1), (2), (4) Date: Dec. 7, 2005

(87) PCT Pub. No.: WO2005/003112

PCT Pub. Date: Jan. 13, 2005

(65) Prior Publication Data

US 2006/0153936 A1    Jul. 13, 2006

(30) Foreign Application Priority Data

Jul. 2, 2003    (JP) .............................. 2003-270377

(51) Int. Cl.
*A01N 65/00* (2006.01)
*A01N 45/00* (2006.01)
*C07D 307/34* (2006.01)

(52) U.S. Cl. ......................... 424/757; 514/26; 514/27; 549/263

(58) Field of Classification Search ................ 424/757, 424/756, 725; 514/27, 26, 33; 549/405, 549/403

See application file for complete search history.

(56) References Cited

FOREIGN PATENT DOCUMENTS

| JP | 6-197734 | 7/1994 |
|---|---|---|
| JP | 8-317762 | 12/1996 |
| JP | 9-117264 | 5/1997 |
| JP | 2001-10963 | 1/2001 |
| JP | 2001-192312 | 7/2001 |
| JP | 2003-195 | 1/2003 |
| JP | 2004-85128 | 3/2004 |
| JP | 2004-91392 | 3/2004 |

OTHER PUBLICATIONS

Schopke, T. et al., "Effects of saponins on the water solubility of quercetin", *Pharmazie*, vol. 52, No. 3, pp. 232 to 234 (1997).
Walthelm, U. et al., "Effects of saponins on the water solubility of different model compounds", *Planta Medica*, vol. 67, No. 1, pp. 49 to 54 (2001).
Mauri, P. et al., "Electrospray characterization of selected medicinal plant extracts", *J. Pharm. Biomed. Anal.*, vol. 23, No. 1, pp. 61 to 68 (2000).
Gallo, F.R. et al., "Propoli: usi e tecniche di rilevazione", *Boll. Chim. Farm.*, vol. 134, No. 9, pp. 483 to 491 (1995).

*Primary Examiner*—D. Margaret Seaman
*Assistant Examiner*—Nizal S Chandrakumar
(74) *Attorney, Agent, or Firm*—Wenderoth, Lind & Ponack, L.L.P.

(57) ABSTRACT

A flavonoid solubilization agent capable of highly solubilizing flavonoids such as isoflavone, baicalin, rutin and naringin whose solubility is generally low; and a method of effecting the above solubilization. Flavonoids can be solubilized by causing a flavonoid and soybean saponin and/or malonyl isoflavone glycoside to be co-present in an aqueous medium.

10 Claims, No Drawings

FLAVONOID SOLUBILIZION AGENT AND METHOD OF SOLUBILIZING FLAVONOID

TECHNICAL FIELD

The present invention relates to a flavonoid solubilizing agent capable of highly solubilizing flavonoids whose solubility is generally low; and a method of effecting the solubilization.

BACKGROUND ART

Patent Document 1: JP 04-27823 B
Patent Document 2: JP 03-27293 A
Patent Document 3: JP 3060227 B2
Patent Document 4: JP 05-176786 A
Patent Document 5: JP 07-107972 A
Patent Document 6: JP 10-101705 A
Patent Document 7: JP 09-309902 A
Patent Document 8: JP 10-298175 A
Patent Document 9: JP 2003-195 A
Non-Patent Document 1: Planta Med, 67 (1), 49-54, 2001

Flavonoids are aromatic compounds whose basic structure is a phenyl chroman skeleton (C6-C3-C6/A ring-C ring-B ring), and are classified into flavones, flavonols, flavanones, flavanonols, isoflavones, anthocyanins, flavanols, chalcones, aurones and the like in accordance with the difference in the C ring moieties. In recent years, as the elucidation of a variety of functionalities of natural components proceeds, the physiological functions of flavonoids have been noted of. However, many of flavonoids are slightly soluble in water, in food products, particularly in drinks and the like, the problems such as cloudiness, sedimentation and the like are caused during the production and storage, and this makes their industrial utilization difficult.

Hitherto, as known methods of solubilizing flavonoids, there are a method of converting isoflavone, rutin, hesperidin or the like into α-glycosyl isoflavonoid, α-glycosyl rutin, α-glycosyl hesperidin or the like by reacting α-glycosyl transferase with it (see Patent Documents 1-3), a method of obtaining catechin glycosides by reacting sucrose phosphorylase with a mixture of catechins and glycose-1-phosphoric acid or sucrose (Patent Document 4), a method of forming glycosides by solubilizing flavonoids in an alkali region of pH 8 or more and/or by addition of a cyclodextrin, and subjecting the solubilized product to glycotransfer with a cyclodextrin synthetic enzyme (Patent Document 5), a method of dissolving flavonoids in strong alkali solution and adding the resultant to a thickening polysaccharide solution (see Patent Document 6), a method of forming an inclusion product of isoflavone with cyclodextrin (Patent Documents 7 and 8) and the like are known.

However, any of the above-described methods is that for solubilizing a specific flavonoid, or that for enhancing the solubility of a specific flavonoid by structure conversion, and is not to provide a method for solubilizing flavonoids in general existing in nature as a basic technology. This is a problem from the viewpoint of versatility. In the methods of Patent Documents 7 and 8, since the solubility of cyclodextrin itself is not so high, the amount to be added is limited, and if a large amount is added, the cyclodextrin forms an inclusion compound with a flavoring agent, etc., and therefore the product design such as flavoring of foods, etc. are hindered.

On the other hand, isoflavones exist mainly in the form of glycosides in legumes and irises. Specifically, there are daidzin, genistin, glycitin, their malonyl glycosides such as 6"-O-malonyl daidzin, 6"-O-malonyl genistin and 6"-O-malonyl glycitin, their acetyl glycosides such as 6"-O-acetyl daidzin, 6"-O-acetyl genistin, 6"-O-acetyl glycitin, their aglycons such as daidzein, genistein and glycitein, and the like. While isoflavones are also in general slightly soluble in water, among them, the malonyl glycosides are known to have relatively soluble nature in water because they have dissociation groups on their side chains. However, it has not been known so far that the malonyl glycosides have an activity of solubilizing isoflavones, much less other flavonoids.

Saponins are classified mainly into steroid saponins and triterpenoid saponins from the viewpoint of their chemical structures. Quillaia saponin, soybean saponin, and enju saponin which are triterpenoid saponins are known to be natural emulsifiers for foods. Patent Document 9 discloses a technology for solubilizing a ginkgo leaf extract containing quercetin, etc. by using saponins together with glycerin, saccharides, etc., and teaches that quillaia saponin is preferred because quillaia saponin is particularly excellent in a surfactant capability. However, since there is a report that saponins are weak in an activity for solublizing a slightly soluble compound in water such as rutin, etc., and in general, should not be used as solubilizing agents (Non-Patent Document 1), it is unknown whether or not saponins have a high activity for solubilizing flavonoids and high versatility, even if their surfactant capability is high.

DISCLOSURE OF THE INVENTION

Problem to be Solved by the Invention

An object of the present invention is to provide a novel method of solubilizing slightly soluble flavonoids.

Means for Solving the Problem

The present inventors have studied intensively the above-described problem. As a result, the present inventors have unexpectedly found that, when having a flavonoid coexist with a soybean saponin or a malonyl isoflavone glycoside in an aqueous medium, the solubility of the flavonoid in water is improved and further, when having a flavonoid coexist with a soybean saponin and a malonyl isoflavone glycoside, the solubility of the flavonoid is further improved depending on a particular kind of a flavonoid. Thus, the present invention has been completed.

That is, the present invention relates to a method of solubilizing flavonoid(s) which comprises having the flavonoid(s) coexist with a soybean saponin and/or a malonyl isoflavone glycoside in an aqueous medium.

EFFECT OF THE INVENTION

The method of the present invention is a quite versatile and easily operable method applicable to solubilization of naturally occurring flavonoids in general which are slightly soluble in water by an easy operation without requiring troublesome processing treatment to obtain a transparent material. Furthermore, since the solubilized flavonoid can be maintained for a long period of time at a lower temperature without formation of a precipitate, the method of the present invention is very advantageous from the viewpoint of storage stability and refrigeration stability.

Function

Although the solubilization mechanism of flavonoids by the method of the present invention has not been elucidated, it is presumed that a soybean saponin would form mixed micelles with flavonoids in an aqueous medium to solubilize the flavonoids. Further, as for a malonyl isoflavone glycoside, it is presumed that the solubilizing force to water would be enhanced by hydrophobic interaction between the aromatic rings each other to increase an affinity for flavonoids. Then, when both components coexist, it is presumed that the solubilizing force would be synergistically enhanced depending on a particular kind of a flavonoid.

BEST MODE FOR CARRYING OUT THE INVENTION

Hereinafter, the present invention will be specifically illustrated. First, examples of the flavonoids in the present invention include flavones (flavone, apigenin, luteolin, biacalein, chrysin and the like), flavonols (kaempferol, quercetin, miricetin and the like), flavanones (hesperetin, naringin, liquiritigenin and the like), flavanolols (alpinone, taxifolin and the like), isoflavones (daidzein, genistein, glycitein, equol, biochanin A, coumestrol, puerarin, formononetin and the like), anthocyanins (pelargonidin, cyanidin, delphinidin, malvidin, petunidin, peonidin, petunidin and the like), flavanols (catechins such as epicatechin, epicatechin gallate, epigallocatechin, epigallocatechin gallate, theaflavin and the like, leukoanthocyanidin and the like), chalcones (carthamine, phloretin and the like), aurones (aurocidine and the like), and the like, their glycosides and analogs. However, the flavonoids are not limited thereto, and the method of the present invention can be widely applied to all flavonoids. These flavonoids in general are slightly soluble in water.

Next, the method of solubilizing flavonoid(s) will be illustrated. For solubilizing flavonoid(s), one can simply have the flavonoid(s) coexist with a soybean saponin and/or a malonyl isoflavone glycoside in an aqueous medium, and it is preferable that both malonyl isoflavone glycoside and soybean saponin are used together, thereby obtaining an excellent solubilizing capability and versatility.

Example of the aqueous medium include water, an aqueous solution of an alcohol, an aqueous solution of an alkali, and an aqueous solution to which saccharides, fruit juices, vegetable juices, vitamins, acidulants, sweetening agents, salts and the like are added. Further, the aqueous medium may be oil-in-water type emulsified emulsions such as milk and the like. Suitably, in order to enhance the solubility of the soybean saponin and flavonoid(s), the aqueous medium preferably has pH of 5 or more, preferably pH 6 to 8.

For having the flavonoid(s) coexist with the soybean saponin and/or the malonyl isoflavone glycoside in the aqueous medium, any method can be employed and examples thereof include a general method such as stirring or homogenizing an aqueous medium containing the flavonoid(s), soybean saponin and/or malonyl isoflavone glycoside.

At this time, in order to enhance the solubility of flavonoid(s) upon coexistence with the soybean saponin and/or the malonyl isoflavone glycoside, preferably, the aqueous medium is subjected to heat treatment, and the heating conditions can be set by taking the solubility of flavonoid(s) to be treated into consideration. Usually, it is sufficient to carry out the heat treatment at 60° C. to 150° C. for about several seconds to about one hour. Needless to say, the heat treatment can be carried out as sterilization during the production steps of a product such as a drink or the like.

In addition, the flavonoid(s) may be previously dissolved in an aliphatic alcohol having 1 to 4 carbon atoms or its solution in a water-containing solvent, an alkali solution or the like, followed by having the dissolved flavonoid(s) coexist with the soybean saponin and the malonyl isoflavone glycoside in the aqueous medium.

The soybean saponin is also referred to as a soyabean saponin, and examples thereof include group A saponin, group B saponin, group E saponin, DDMP saponin and the like. Its structure is different from that of a quillaia saponin or the like. In the present invention, these saponins may be used alone or in combination. Among them, group A saponin is bis-desmoside saponin, and its solubilizing capability is particularly high. Then, it is preferable that 50% or more of the soybean saponin to be used is group A saponin. Therefore, although a method of preparing a material containing a soybean saponin to be used in the present invention is not particularly limited, most preferably, soybean hypocotyls are extracted with a solvent such as water, water-containing alcohol or the like, followed by being appropriately purified. Further, the present invention also includes the use of a composition mainly containing a soybean saponin and, for example, commercially available "Soy Health SA" which contains about 50% of soybean saponin (among them, about 33% is group A saponin) (manufactured by Fuji Oil Company, Limited) and the like can be used.

As a malonyl isoflavone glycoside, for example, 6"-O-malonyl daidzin, 6"-O-malonyl genistin, 6"-O-malonyl glycitin and the like can be used alone or in combination. Since these malonyl isoflavone glycosides have malonyl group in their side chains, these malonyl isoflavone glycosides have the nature of being relatively soluble in water among these isoflavones. Although a method of preparing a malonyl isoflavone glycoside is not particularly limited, soybean hypocotyls are extracted with a solvent such as water, water-containing alcohol or the like, followed by being appropriately purified. Further, of course, the present invention includes the use of a composition mainly containing a malonyl isoflavone glycoside and, for example, commercially available "Soya Flavone HG" containing about 20% of a malonyl isoflavone glycoside (manufactured by Fuji Oil Company, Ltd.) can be used.

Suitably, the amount of a soybean saponin to be used is 5% by weight or more, more preferably 30 to 300% by weight as dry weight ratio relative to the flavonoid(s). If the amount to be added small, the flavonoid(s) are insufficiently solubilized, and on the contrary, if the amount to be added is too large, it is uneconomical.

In the case where a soybean saponin and a malonyl isoflavone glycoside are used in combination, suitably, the amount of the soybean saponin and the malonyl isoflavone glycoside to be used is 5% by weight or more, more preferably 30 to 300% by weight as dry weight ratio relative to the flavonoid(s).

The amount of the flavonoid(s) to be used can be appropriately adjusted in accordance with the purpose, however, in order to obtain the maximum dissolution of flavonoid(s), an excessive amount of flavonoid(s) are added to and saturated in the aqueous medium, and then the solid matter can be removed by filtering and so on. Flavonoid(s) which have been solubilized in this way are transparently dissolved and are also excellent in stability in the aqueous medium. In the case that sufficient stability is also required under refrigeration conditions, preferably, a mixture of flavonoids(s), a soybean saponin and/or a malonyl isoflavone glycoside is previously cooled to a lower temperature prior to filtration of the solid matter.

The above-described solubilization method can be used in the production steps of the following products, thereby solubilizing the flavonoid(s) to obtain flavonoid-containing products having high storage stability.

Further, there can be provided as a flavonoid solubilizing agent by utilizing the solubilizing capability of a soybean saponin and/or a malonyl isoflavone glycoside, that is, by utilizing these pure materials or a preparation containing them as such, or optionally together with additives such as a saccharide, emulsifier and the like. This flavonoid solubilizing agent can be provided by processing it into a variety of forms such as powder, liquid and the like.

Moreover, there can be provided a solubilized flavonoid composition by utilizing the flavonoid solubilizing capability of a soybean saponin and/or a malonyl isoflavone glycoside, having flavonoid(s) coexist with a soybean saponin and/or a malonyl isoflavone glycoside in an aqueous medium and, if necessary, subjecting the resultant mixture to heat treatment to obtain a solubilized flavonoid solution. The solution as such or after processing it into powder can be used as the composition. Since the obtained solubilized flavonoid composition is extremely high in water-solubility at ordinary temperature, it can be added as it is and utilized during the production of a variety of products, particularly liquid products, for example, foods and drinks, medicines, quasi drugs, cosmetics, oral preparations, dentifrices, aromatic agents, deodorants, detergents and the like. Among these, it is advantageous to utilize the composition for healthy foods and drinks to which a variety of physiological functions that flavonoids have are given.

Hereinafter, Examples will be described, however, the technological concept of the present invention is not limited to these exemplifications.

EXAMPLE 1

Ultrapure water 10 mL was added to commercially available baicalin (flavones, purity; 90% or more, manufactured by Wako Pure Chemicals, Co., Ltd.) 100 mg, and a commercially available malonyl glycoside-rich soybean isoflavone (trade name "Soya Flavone HG", manufactured by Fuji Oil Company, Limited) 100 mg as a solubilizing agent (containing 20 mg of soybean saponin, 15 mg of group A saponin, and 20 mg of malonyl isoflavone glycoside), or a commercially available soybean saponin (trade name "Soy Health SA", manufactured by Fuji Oil Company, Limited) 100 mg (containing 50 mg of soybean saponin, and 33 mg of group A saponin), and the mixture was stirred at 80° C. for one hour. Then, after the mixture was equilibrated at 10° C. for 48 hours, the supernatant was collected by centrifugation. The $OD_{254}$ of the supernatant was measured and the dissolution amount of baicalin was calculated by the following equation 1.

baicalin dissolution amount (mg/100 mL)=($OD_{254}$ in sample supernatant−$OD_{254}$ in control supernatant)/baicalin specific absorbance×1000

Further, the supernatant was placed in a test tube and, after it was pasteurized by heating at 95° C. for 15 minutes, it was stored at 10° C. for one month to observe the formation of a precipitate by visual examination.

TABLE 1

| Solubilizing agent | Baicalin dissolution amount (mg/100 mL) | Storage stability (10° C.) |
| --- | --- | --- |
| without additive | 12.4 | precipitate |
| Soya Flavone HG | 130.6 | no precipitate |
| Soy Health SA | 75.9 | no precipitate |

The soybean saponin, or the soybean saponin and the malonyl isoflavone showed a high solubilizing capability with respect to baicalin. The solubilizing magnifying power indicated 10.5-fold in the co-presence of the soybean saponin/the malonyl isoflavone glycoside relative to baicalin alone, and indicated 6.1-fold in the co-presence of the soybean saponin. The baicalin solution thus solubilized showed excellent stability without formation of a precipitate during storage under refrigeration.

EXAMPLE 2

Ultrapure water 10 mL was added to commercially available rutin (flavonols, purity: 90% or more, manufactured by Wako Pure Chemicals, Co., Ltd.) 100 mg and the same solubilizing agent as that used in Example 1, and the mixture was stirred at 80° C. for one hour. Then, after it was equilibrated at 10° C. for 48 hours, the supernatant was collected by centrifugation. The $OD_{254}$ of the supernatant was measured and a rutin dissolution amount was calculated by the following equation 2.

rutin dissolution amount (mg/100 mL)=($OD_{254}$ in sample supernatant−$OD_{254}$ in control supernatant)/rutin specific absorbance×1000

Further, the supernatant was placed in a test tube, after it was pasteurized by heating at 95° C. for 15 minutes, it was stored at 10° C. for one month to observe the formation of a precipitate by visual examination.

TABLE 2

| Solubilizing agent | Rutin dissolution amount (mg/100 mL) | Storage stability (10° C.) |
| --- | --- | --- |
| without additive | 3.0 | precipitate |
| Soya Flavone HG | 90.3 | no precipitate |
| Soy Health SA | 117.7 | no precipitate |

The soybean saponin, or the soybean saponin and the malonyl isoflavone showed a high solubilizing capability with respect to rutin. The solubilizing magnifying power indicated 30.1-fold in the co-presence of the soybean saponin/the malonyl isoflavone glycoside relative to rutin alone, and indicated 39.2-fold in the co-presence of the soybean saponin. The rutin solution thus solubilized showed excellent stability without formation of a precipitate during the storage.

EXAMPLE 3

Ultrapure water 10 mL was added to commercially available hesperidin (flavanones, purity: 92% or more, manufactured by Wako Pure Chemicals, Co., Ltd.) 100 mg and the same solubilizing agent as that used in Example 1, and the mixture was stirred at 80° C. for one hour. Then, after it was equilibrated at 10° C. for 48 hours, the supernatant was collected by centrifugation. The $OD_{254}$ of the supernatant was measured and a hesperidin dissolution amount was calculated by the following equation 3.

hesperidin dissolution amount (mg/100 mL)=($OD_{254}$ in sample supernatant−$OD_{254}$ in control supernatant)/hesperidin specific absorbance×1000

Further, the supernatant was placed in a test tube, and after it was pasteurized by heating at 95° C. for 15 minutes, it was stored at 10° C. for one month to observe the formation of a precipitate by visual examination.

TABLE 3

| Solubilizing agent | Hesperidin dissolution amount (mg/100 mL) | Storage stability (10° C.) |
| --- | --- | --- |
| without additive | 8.6 | precipitate |
| Soya Flavone HG | 78.0 | no precipitate |
| Soy Health SA | 78.0 | no precipitate |

The soybean saponin, or the soybean saponin and the malonyl isoflavone showed a high solubilizing capability with respect to hesperidin. The solubilizing magnifying power indicated 9.1-fold in the co-presence of the soybean saponin/the malonyl isoflavone glycoside with respect to hesperidin alone, and indicated 9.1-fold in the co-presence of the soybean saponin. The hesperidin solution thus solubilized showed excellent stability without formation of a precipitate during the storage.

EXAMPLE 4

Ultrapure water 10 mL was added to commercially available naringin (flavanones, purity: 95% or more, manufactured by Sigma Inc.) 100 mg and the same solubilizing agent as that used in Example 1, and the mixture was stirred at 80° C. for one hour. Then, after it was equilibrated at 10° C. for 48 hours, the supernatant was collected by centrifugation. The $OD_{254}$ in the supernatant was measured and a naringin dissolution amount was calculated by the following equation 4.

naringin dissolution amount (mg/100 mL)=($OD_{254}$ in sample supernatant−$OD_{254}$ in control supernatant)/naringin specific absorbance×1000

Further, the supernatant was placed in a test tube, and after it was pasteurized by heating at 95° C. for 15 minutes, it was stored at 10° C. for one month to observe the formation of a precipitate by visual examination.

TABLE 4

| Solubilizing agent | Naringin dissolution amount (mg/100 mL) | Storage stability (10° C.) |
| --- | --- | --- |
| without additive | 68.0 | precipitate |
| Soya Flavone HG | 975.0 | no precipitate |
| Soy Health SA | 980.0 | no precipitate |

The soybean saponin or the soybean saponin and the malonyl isoflavone showed a high solubilizing capability with respect to naringin. The solubilizing magnifying power indicated 14.3-fold in the co-presence of the soybean saponin/the malonyl isoflavone glycoside with respect to naringin alone, and indicated 14.4-fold in the co-presence of the soybean saponin. The naringin solution thus solubilized showed excellent stability without formation of a precipitate during the storage.

EXAMPLE 5

Ultrapure water 10 mL was added to a commercially available soybean isoflavone (trade name "Honen Isoflavone-80", manufactured by Honen Corporation) 125 mg (100 mg of isoflavone glycoside) and the same solubilizing agent as used in Example 1 and the mixture was stirred at 80° C. for one hour. Then, after it was equilibrated at 10° C. for 48 hours, the supernatant was collected by centrifugation and an isoflavone dissolution amount was measured by HPLC. Further, the supernatant was placed in a test tube, and after it was pasteurized with heating at 95° C. for 15 minutes, it was stored at 10° C. for one month to observe the formation of a precipitate by visual examination.

TABLE 5

| Solubilizing agent | Isoflavone amount (mg/100 mL) | Storage stability (10° C.) |
| --- | --- | --- |
| without additive | 25.6 | precipitate |
| Soya Flavone HG | 698.4 | no precipitate |
| Soy Health SA | 215.8 | no precipitate |

The soybean saponin, or the soybean saponin and the malonyl isoflavone indicated a high solubilizing capability with respect to the isoflavone (slightly soluble isoflavone other than malonyl isoflavone glycoside). The solubilizing magnifying power indicated 27.3-fold in the co-presence of the soybean saponin/the malonyl isoflavone glycoside, and indicated 84.4-fold in the co-presence of the soybean saponin with respect to the isoflavone alone. The isoflavone solution thus solubilized showed excellent stability without formation a precipitate during the storage.

EXAMPLE 6

Ultrapure water 1 mL was added to a commercially available soybean isoflavone (trade name "Honen Isoflavone-80", manufactured by Honen Corporation) 12.5 mg (10 mg of isoflavone glycoside) and a commercially available malonyl isoflavone glycoside, malonyl daidzin (purity: 90% or more, manufactured by Wako Pure Chemicals, Co., Ltd.) 1 mg, and the mixture was stirred at 25° C. for one hour. Then, after it was equilibrated at 10° C. for 48 hours, the supernatant was collected by centrifugation and an isoflavone dissolution amount was measured by HPLC. Further, the supernatant was placed in a test tube, it was stored as such at 10° C. for one month to observe the formation of a precipitate by visual examination.

TABLE 6

| Solubilizing agent | Isoflavone amount (mg/100 mL) | Storage stability (10° C.) |
| --- | --- | --- |
| without additive | 17.3 | precipitate |
| Malonyl daidzin | 106.3 (including 56.9 of malonyl daidzin) | No precipitate |

One of malonyl isoflavones, i.e., malonyl diazin alone also showed a high solubilizing capability with respect to the isoflavone glycoside. Since the dissolution amount of malonyl daidzin itself is 56.9 mg/100 mL, the solubilizing magnifying power of the isoflavone glycoside indicated 2.9-fold in the co-presence of malonyl daidzin. The isoflavone solution thus solubilized showed excellent effect stability without formation of a precipitate during the storage.

EXAMPLE 7

Ultrapure water 10 mL was added to a commercially available soybean isoflavone (trade name "Honen Isoflavone-80", manufactured by Honen Corporation) 125 mg (100 mg of isoflavone glycoside) and the same commercially available malonyl-rich soybean isoflavone as that used in Example 1, 100 mg, 300 mg, or 1000 mg, or the same commercially available soybean saponin as that used in Example 1, 100 mg, 300 mg, or 1000 mg, and the mixture was stirred at 80° C. for one hour. Subsequently, after it was equilibrated at 10° C. for 48 hours, the supernatant was collected by centrifugation and an isoflavone dissolution amount was measured by HPLC. Further, the supernatant was placed in a test tube, and after it was pasteurized by heating at 95° C. for 15 minutes, it was stored at 10° C. for one month to observe the formation of a precipitate by visual examination.

TABLE 7

| Solubilizing agent | Malonyl isoflavone glycoside content (mg/100 mL) | Soybean saponin content (mg/10 mL) | Isoflavone dissolution amount (mg/100 mL) | Storage stability (10° C.) |
|---|---|---|---|---|
| without additive | 0 | 0 | 25.6 | precipitate |
| Soya Flavone HG | 20 | 20 | 697.2 | no precipitate |
| | 60 | 60 | 1502.3 | no precipitate |
| | 200 | 200 | 4405.6 | no precipitate |
| Soy Health SA | 0 | 50 | 213.7 | no precipitate |
| | 0 | 150 | 329.4 | no precipitate |
| | 0 | 500 | 764.9 | no precipitate |

The malonyl isoflavone or the soybean saponin showed a solubilizing capability with respect to the isoflavone (slightly soluble isoflavone other than malonyl isoflavone) in a concentration-dependent manner. The solubilizing magnifying power indicated 172-fold at maximum in the co-presence of the malonyl isoflavone and 30-fold at maximum in the co-presence of the soybean saponin. The isoflavone solution thus solubilized showed excellent without formation of a precipitate during the storage.

EXAMPLE 8

The capability of a soybean saponin and quillaia saponin, used as a surfactant, for solubilizing a variety of flavonoids, was compared. A commercially available soybean saponin powder ("Soy Health SA", manufactured by Fuji Oil Company, Limited) or dry powder of a commercially available quillaia saponin liquid preparation ("Quillaianin S-100", manufactured by Maruzen Pharmaceuticals, Co., Ltd.) 0.1 g, and an isoflavone (glycoside), rutin or ginkgo leaf extract (containing quercetin, kaempferol, and the like) 0.01 g were placed in a test tube. After 0.2 M Na2HPO4/0.1 M acetic acid buffer (pH7) 10 mL was added thereto and stirred, the mixture was pasteurized with heating in a boiling water bath for 15 minutes. Then, after it was stored at 10° C. for 2 weeks, the dissolution state of the liquid thus obtained was observed by visual observation.

As a result, as shown in Table 8, the soybean saponin clearly solubilized all of the isoflavone, rutin, and ginkgo leaf extract. On the other hand, quillaia saponin solubilized only ginkgo leaf extract. Hence, it was unexpectedly found that a solubilizing capability of the soybean saponin with respect to the flavonoid was superior to that of quillaia saponin and the versatility of the soybean saponin was higher than that of quillaia saponin.

TABLE 8

| Flavonoids | Solubilizing agent addition-free | Soybean saponin | Quillaia saponin |
|---|---|---|---|
| Isoflavone | x | o | x |
| Rutin | x | o | x |
| Ginkgo leaf extract | x | o | o | o: precipitate
x: no precipitate

INDUSTRIAL APPLICABILITY

The solubilization of flavonoids in general can be easily performed in a high degree without changing their chemical structures and physiological effects by utilizing a soybean saponin and/or a malonyl isoflavone glycoside as a solubilizing agent of the flavonoids. The present invention can provide a highly versatile basic technology of flavonoid solubilization. Hence, it can be utilized particularly for wide range of products which are used by dissolving flavonids, such as foods and drinks, medicines, quasi drugs, cosmetics, oral preparations, dentifrices, aromatic agents, deodorants, detergents and the like.

The invention claimed is:

1. A method of solubilizing flavonoid(s) which comprises having the flavonoid(s) coexist with a soybean saponin whose group A saponin content is 50% or more and/or a malonyl isoflavone glycoside in an aqueous medium.

2. The solubilizing method according to claim 1, wherein the flavonoid(s) are one or more flavonoids selected from flavones, flavonols, flavanones, flavanonols, isoflavones, anthocyanins, flavanols, chalcones, and aurones.

3. A flavonoid solubilizing agent comprising a soybean saponin whose group A saponin content is 50% or more and/or a malonyl isoflavone glycoside.

4. A solubilized flavonoid composition obtainable by having flavonoid(s) coexist with a soybean saponin whose group A saponin content is 50% or more and/or a malonyl isoflavone glycoside in an aqueous medium.

5. A flavonoid-containing product comprising the solubilized flavonoid composition according to claim 4.

6. The flavonoid-containing product according to claim 5, which is a food or drink, a medicine, a cosmetic, an oral preparation, a dentifrice, an aromatic agent, a deodorant, or a detergent.

7. The flavonoid-containing food or drink according to claim 6, which has the physiological function(s) of the flavonoid(s).

8. A process for producing a flavonoid-containing product, which comprises the steps of adding flavonoid(s), and a soybean saponin whose group A saponin content is 50% or more and/or a malonyl isoflavone glycoside to an aqueous medium; and then subjecting the resulting mixture to heat treatment to solubilize the flavonoid(s).

9. The process according to claim 8, wherein the flavonoid-containing product is a food or drink, a medicine, a cosmetic, an oral preparation, a dentifrice, an aromatic agent, a deodorant, or a detergent.

10. The process for producing a flavonoid-containing food or drink according to claim 8, to which the physiological function(s) of the flavonoid(s) have been imparted.

* * * * *